United States Patent [19]
Jonas et al.

[11] Patent Number: 5,206,363
[45] Date of Patent: Apr. 27, 1993

[54] PROCESS FOR THE RESOLUTION OF ENANTIOMERS OF 5-HETEROARYL-1,3,4-THIADIAZINONES

[75] Inventors: Rochus Jonas, Darmstadt; Peter Ersing, Stockstadt, both of Fed. Rep. of Germany

[73] Assignee: Merck Patent Gesellschaft Mit Beschrankter Haftung, Darmstadt, Fed. Rep. of Germany

[21] Appl. No.: 939,754

[22] Filed: Sep. 2, 1992

[30] Foreign Application Priority Data

Sep. 2, 1991 [DE] Fed. Rep. of Germany ....... 4129062

[51] Int. Cl.$^5$ .................. C07D 285/16; C07D 417/02
[52] U.S. Cl. ......................................... 540/593; 544/8
[58] Field of Search ............................ 540/593; 544/8

[56] References Cited
PUBLICATIONS

Jonas et al., Chemical Abstracts, vol. 110, entry 192866w (1989).

*Primary Examiner*—John M. Ford
*Attorney, Agent, or Firm*—Millen, White, Zelano & Branigan

[57] ABSTRACT

The invention relates to a process for the resolution of enantiomers of 5-heteroaryl-1,3,4-thiadiazinones of formula I by the kinetic resolution of racemates, characterized in that racemic I is dissolved in an inert solvent or solvent mixture and acylated with a chiral acid chloride. The resulting mixture of diastereoisomers is reacted with an amine or alcohol, thereby achieving a complete resolution of one of the diastereoisomers and a very slight or partial resolution of the other diastereoisomer into the enantiomers on which they are based, the resolution products are then separated off and the remaining pure diastereoisomer is converted to the corresponding pure enantiomer by reaction with an amine or an alcohol.

22 Claims, No Drawings

PROCESS FOR THE RESOLUTION OF ENANTIOMERS OF 5-HETEROARYL-1,3,4-THIADIAZINONES

SUMMARY OF THE INVENTION

The invention relates to a process for the resolution of enantiomers of 5-heteroaryl-1,3,4-thiadiazinones of formula I:

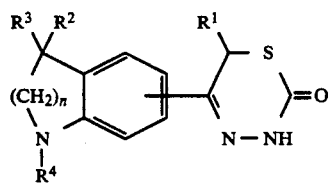

wherein
$R^1$ is A,
$R^2$ and $R^3$ are each H or A,
$R^4$ is H, A or acyl having 1-15 C atoms,
A is alkyl having 1-8 C atoms and
n is 1, 2 or 3.

Thiadiazinone derivatives of formula I are known from European patent 0 294 647 and have the meanings indicated therein as preferred.

Above and below, $R^1$ to $R^4$ and A are as defined for formula I, unless expressly indicated otherwise.

In the formulae, alkyl is preferably unbranched, has preferably 1, 2 or 3 C atoms and is preferably methyl, or preferably ethyl or propyl, or else preferably isopropyl, butyl, isobutyl, sec-butyl, tert- butyl, n-pentyl or isopentyl.

Acyl is the acid radical of a carboxylic or sulfonic acid, preferably alkanoyl having 1-10 or especially 1, 2, 3, 4 or 5 C atoms, specifically preferably acetyl, or preferably formyl, propionyl, butyryl, isobutyryl, valeryl, isovaleryl or pivaloyl (trimethylacetyl), or else preferably substituted or unsubstituted aroyl having 7-15 C atoms, possible substituents being especially 1-3 or preferably one of the following groups: alkyl, alkoxy, alkylthio, alkylsulfinyl or alkylsulfonyl each having 1-3 or preferably 1 or 2 C atoms, methylenedioxy and also OH, F, Cl, Br, I, $NO_2$, $NH_2$ and alkylamino or dialkylamino each having 1-3 or preferably 1 or 2 C atoms in the alkyl group. Specific preferred aroyl radicals are benzoyl, o-, m- or p- toluyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylthiobenzoyl, o-, m- or p-methylsulfinylbenzoyl, o-, m- or p-methylsulfonylbenzoyl, 2,3- or 3,4-methylenedioxybenzoyl and 1- or 2-naphthoyl. Acyl can also be heteroarylcarbonyl having 2-10 C atoms, such as 2- or 3-furoyl, 2- or 3-thenoyl, picolinoyl, nicotinoyl or isonicotinoyl, or else arylalkanoyl such as phenylacetyl, o-, m- or p-methoxyphenylacetyl, 2- or 3-phenylpropionyl or 2-, 3- or 4-phenylbutyryl, cycloalkylcarbonyl such as cyclohexylcarbonyl, alkylsulfonyl such as methyl-, ethyl-, propyl- or butyl-sulfonyl, or arylsulfonyl such as benzenesulfonyl, o-, m- or p- toluenesulfonyl, o-, m- or p-methoxybenzenesulfonyl or 1- or 2-naphthalenesulfonyl.

Resolution of the racemate into the respective enantiomers has hitherto been possible only by means of expensive HPLC processes.

An object of the invention s to provide a process for the resolution of enantiomers of formula I which avoids an expensive HPLC resolution with a small through-put of substance, but simultaneously produces a high enantiomeric purity in satisfactory amounts of substances.

Upon further study of the specification and appended claims, further objects and advantages of this invention will become apparent to those skilled in the art.

These objects are achieved by the discovery of the present process, namely the kinetic resolution of racemates, in respect of the resolution of enantiomers of 5-heteroaryl-1,3,4-thiadiazinones.

The invention accordingly relates to a process for the resolution of enantiomers of Formula I, characterized in that racemic I is dissolved in an inert solvent or solvent mixture and acylated with a chiral acid chloride, the resulting mixture of diastereoisomers is reacted with an amine or alcohol, thereby achieving a complete resolution of one of the diastereoisomers and possibly a very slight or partial resolution of the other diastereoisomer into the enantiomers on which they are based, the resolution products are then separated off and the remaining pure diastereoisomer is converted to the corresponding pure enantiomer by reaction with an amine or an alcohol.

If a partial resolution of the other diastereoisomer occurs, such a partial resolution can amount to, for example, 0.01-0.99% of the total of the other diastereoisomer.

Racemic I refers to a racemic mixture of enantiomers of Formula I.

The process of the kinetic resolution of racemates does not normally produce a satisfactory enantiomeric purity and has to be supplemented by additional processes.

It is therefore surprising that this process can be applied successfully in the case of compounds of Formula I and produces an enantiomeric purity of more than 99% in all Examples without the use of supplementary methods.

Suitable solvents are preferably ethers such as tetrahydrofuran (THF), dioxane or methyl tert.-butyl ether, hydrocarbons such as hexane, cyclohexane, benzene, toluene, xylenes or mesitylene, glycol dialkyl ethers such as glycol dimethyl or diethyl ether, amides such as dimethylformamide (DMF), halogenated hydrocarbons such as methylene chloride, chlorobenzene or trichloroethylene, and mixtures of these solvents.

Methylene chloride and THF are particularly preferred.

Examples of suitable optically active acid chlorides are tetrahydro-5-oxofuran-2-carboxylic acid chloride, o-acetylmandelic acid chloride, campholic acid chloride or, particularly preferably, camphanic acid chloride.

Specifically, racemic I is dissolved or suspended in one of said solvents or a solvent mixture, a base is conveniently added and the acid chloride, dissolved in one of said solvents or in the pure form, is added. Examples of suitable bases are alkali metal or alkaline earth metal hydroxides, carbonates and alcoholates, but especially secondary or tertiary amines such as, for example, triethylamine or pyridine. The reaction mixture is then stirred for 1-48 hours at temperatures of between −20° and the boiling point of the solvent, preferably in the range from −10° to +30°, and the mixture of diastereoisomers is isolated. To resolve the mixture of diastereoisomers, said mixture is redissolved in one of said solvents, treated with an amine or an alcohol and again stirred for 1–48 hours at 0°–50°, preferably at 0°–30°, or simply left to stand.

It is equally possible to dissolve the mixture of diastereoisomers directly in a suitable alcohol without using an additional solvent.

Examples of suitable alcohols are lower alcohols having 1–8 C atoms, especially methanol, ethanol or isopropanol, but also mixtures thereof. Suitable amines are inter alia piperidine, pyrrolidine, morpholine or else ethylamine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 29 062.3, filed Sep. 2, 1991, are hereby incorporated by reference.

EXAMPLES

In the following Examples, which serve to illustrate the invention in greater detail, all temperatures are given in ° C., as in the preceding text. "Conventional working-up" means that water or dilute sodium hydroxide solution is added if necessary, the mixture is extracted with an organic solvent such as ethyl acetate, chloroform or methylene chloride, the organic phase is separated off, dried over $Na_2SO_4$ or $MgSO_4$, filtered and evaporated and the residue is additionally purified by chromatography or crystallization if appropriate. The enantiomeric purity can be determined for example by HPLC or differential scanning calorimetry (DSC). The abbreviations HPLC and ee stand for high pressure liquid chromatography and enantiomeric excess.

EXAMPLES

Example 1

A solution of 26 g of (−)-camphanic acid chloride in 100 ml of methylene chloride is added dropwise at 0°, with stirring, to a suspension of 48 g of 5-[1- (3,4-methylenedioxybenzoyl)-1,2,3, 4-tetrahydroquinol-6-yl]-6-methyl-3,6-dihydro-2H-1,3,4-thiadiazin-2-one in 800 ml of methylene chloride to which 20 ml of triethylamine have been added, and the reaction mixture is stirred for 4 hours. It is then washed with dilute hydrochloric acid and subsequently with bicarbonate solution. The organic phase is separated off and worked up in conventional manner to give 3-[(−)-camphanoyl]-5-[1-(3,4-methylenedioxybenzoyl)-1,2,3, 4- tetrahydroquinol-6-yl]-6-methyl-3,6-dihydro-2H-1,3,4- thiadiazin-2-one as a mixture of diastereoisomers, m.p. 216°–217°.

Example 2

48 g of the mixture of diastereoisomers of Example 1 are dissolved in 800 ml of tetrahydrofuran, 3.6 ml of morpholine are added and the reaction mixture is left to stand for 14 hours at 25°. It is concentrated, aqueous ethyl acetate is added and the mixture is worked up in conventional manner. The (−)-enantiomer obtained by resolution, which is contaminated with small amounts of (+)-enantiomer, is separated from the bulk of the unresolved diastereoisomer by chromatography. The small amount of (+)-enantiomer present is removed from the (−)-enantiomer as the racemate by recrystallization from ethanol. Concentration of the mother liquor and crystallization gives (−)-5-[1-(3,4- methylenedioxybenzoyl)-1,2,3,4-tetrahydroquinol-6-yl]- 6-methyl-3, 6-dihydro-2H-1,3,4-thiadiazin-2-one, m.p. 180°; $[\alpha]_D^{20} = -534.2°$; ee>99% (HPLC).

Example 3

20 g of the unresolved diastereoisomer of Example 2 are dissolved in THF, 3 ml of morpholine are added and the mixture is processed further analogously to Example 2. After removal of the solvent, the residue is recrystallized from ethanol to give (+)-5-[1- (3,4-methylenedioxybenzoyl)-1,2,3, 4-tetrahydroquinol-6-yl]-6-methyl-3,6-dihydro-2H-1,3,4-thiadiazin-2-one, m.p. 181°; $[\alpha]_D^{20} = ++541.5°$; ee>99%.

Example 4

20 g of the unresolved diastereoisomeric compound of Example 2 are dissolved in 400 ml of methanol and boiled for 24 hours. After removal of the solvent, the residue is recrystallized from ethanol to give (+)- 5-[1-(3,4-methylenedioxybenzoyl)-1,2,3, 4-tetrahydroquinol-6-yl]-6-methyl-3,6-dihydro-2H-1,3,4-thiadiazin-2-one, m.p. 181°; $[\alpha]_D^{20} = ++541.5°$; ee>99%.

Example 5

Analogously to Example 1, the racemic mixture of 5-[1-methyl-1,2,3,4-tetrahydroquinol-6-yl]-6-methyl-3,6-dihydro-2H-1,3,4-thiadiazin-2 H-1,3,4-thiadiazin-2-one (m.p. 177°) is reacted with (+)-camphanic acid chloride to give 3- [(+)-camphanoyl]-5-(1-methyl-1,2,3, 4-tetrahydroquinol-6-yl)-6-methyl-3,6-dihydro-2H-1,3,4-thiadiazin-2-one as a mixture of diastereoisomers.

Example 6

The mixture of diastereoisomers of Example 5 is reacted with morpholine analogously to Example 2 to give (+)-5-(1-methyl-1,2,3,4-tetrahydroquinol-6-yl)-6-methyl-3,6-dihydro-2H-1,3, 4-thiadiazin-2-one and the corresponding unresolved diastereoisomer, the further processing of which is described in Example 7.

Example 7

The unresolved diastereoisomer of Example 6 is dissolved in methanol and boiled for 20 hours, analogously to Example 4. After removal of the solvent, the residue is recrystallized from ethanol to give (−)-5-(1-methyl-1,2,3,4-tetrahydroquinol-6-yl)-6-methyl-3,6-dihydro-2H-1,3, 4-thiadiazin-2-one.

Example 8

Analogously to Example 1, the racemate of 5-[1-(3,4,5-trimethoxybenzyl)-1,2,3, 4-tetrahydroquinol-6-yl]-6-methyl-3,6-dihydro-2H-1,3,4-thiadiazin-2-one is reacted with (−)-camphanic acid chloride to give 3-[(+)-camphanoyl]-5-[1-(3,4, 5-trimethoxybenzoyl)-1,2,3,4,-tetrahydroquinol-6-yl]-6-methyl-3,6-dihydro-2H- 1,3, 4-thiadiazin-2-one as a mixture of diastereoisomers.

3-[(+)-Camphanoyl]-5-[1-isonicotinoyl-2,3,4, 5-tetrahydro-1H-1-benzazepin-7-yl]-6-methyl-3,6-dihydro-2H-1,3,4-thiadiazin-2-one as a mixture of diastereomers is obtained analogously.

Example 9

The mixture of diastereoisomers of Example 8 is reacted with morpholine analogously to Example 2 to give (−)-5- [1- (3,4,5-trimethoxybenzoyl)-1,2,3,4-tetrahydroquinol-6-yl]-6-methyl-3, 6-dihydro-2H-1,3,4-thiadiazin-2-one and the corresponding unresolved diastereoisomer, the further processing of which is described in Example 10.

(−)-5-[1-Isonicotinoyl-2,3,4,5-tetrahydro-1H-1-benzazepin-7-yl]-6-methyl-3, 6-dihydro-2H-1,3,4-thiadiazin-2-one is obtained analogously.

Example 10

Analogously to Example 3, (+)-5-[1-(3,4,5-trimethoxybenzoyl)-1,2,3, 4-tetrahydroquinol-6-yl]-6-methyl-3,6-dihydro-2H-1,3,4-thiadiazin-2-one, $[\alpha]_D^{20} = +476.2°$, is obtained starting from the unresolved diastereoisomer of Example 9.

(+)-5-[1-Isonicotinoyl-2,3,4,5-tetrahydro-1H-1-benzazepin-7-yl]-6-methyl-3, 6-dihydro-2H-1,3,4-thiadiazin-2-one, $[\alpha]_D^{20} = +478.2°$, is obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the resolution of enantiomers of 5-heteroaryl-1,3,4-thiadiazinones of formula I:

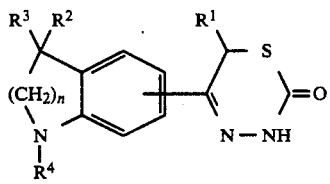

wherein
R$^1$ is A,
R$^2$ and R$^3$ are each H or A,
R$^4$ is H, A or acyl having 1–15 C atoms,
A is alkyl having 1–8 C atoms and
n is 1, 2 or 3,
by kinetic resolution of a racemate thereof, said process comprising:
dissolving a racemate of a compound of Formula I in an inert solvent or inert solvent mixture;
reacting said racemate with a chiral acid chloride;
reacting the resulting mixture of diastereoisomers with an amine or alcohol, thereby achieving a complete resolution of one of the diastereoisomers and a partial resolution of the other diastereoisomer into the enantiomers on which they are based;
separating the resolved enantiomer from the unresolved diastereomer;
converting the unresolved diastereoisomer into its corresponding enantiomer by reaction with an amine or alcohol.

2. A process according to claim 1, wherein the resulting mixture of diastereoisomers is reacted with an alcohol.

3. A process according to claim 2, wherein said unresolved diastereoisomer is reacted with an alcohol.

4. A process according to claim 1, wherein the resulting mixture of diastereoisomers is reacted with an amine.

5. A process according to claim 4, wherein said unresolved diastereoisomer is reacted with an amine.

6. A process according to claim 1, wherein said inert solvent or inert solvent mixture is an ether, a hydrocarbon solvent, a glycol dialkyl ether, an amide, a halogenated hydrocarbon or mixture thereof.

7. A process according to claim 1, wherein said inert solvent or said inert solvent mixture is selected from the group consisting of tetrahydrofuran, dioxane, methyl tert.-butyl ether, hexane, cyclohexane, benzene, toluene, xylene, mesitylene, glycol dimethyl ether, glycol diethyl ether, dimethylformamide, methylene chloride, chlorobenzene, trichloroethylene, or mixtures thereof.

8. A process according to claim 1, wherein said inert solvent or inert solvent mixture is methylene chloride, tetrahydrofuran, or a mixture thereof.

9. A process according to claim 1, wherein said chiral acid chloride is tetrahydro-5-oxofuran-2-carboxylic acid chloride, o-acetylmandelic acid chloride, campholic acid chloride or camphanic acid chloride.

10. A process according to claim 9, wherein said acid chloride is camphanic acid chloride.

11. A process according to claim 1, wherein said inert solvent or inert solvent mixture further contains a base.

12. A process according to claim 1, wherein said alcohol is an alcohol having 1–8 carbon atoms or mixtures thereof.

13. A process according to claim 1, wherein said alcohol is methanol, ethanol, isopropanol or mixtures thereof.

14. A process according to claim 1, wherein said amine is piperidine, pyrrolidine, morpholine or ethylamine.

15. A process according to claim 1, wherein said racemate of compound of formula I is a racemate of compounds according to the formula 5-[1-R$^4$-1,2,3,4-tetrahydroquinol-6-yl]-6-methyl-3,6-dihydro-2H-1, 3,4-thiadiazin-2-one.

16. A process according to claim 1, wherein said racemate of compound of formula I is a racemate of compounds according to the formula 5-[1-R$^4$-2,3,4,5-tetrahydro-1H-1-benzazepin-7-yl ]-6-methyl-3,6-dihydro-2H-1,3,4-thiadiazin-2-one.

17. A process according to claim 1, wherein R$^1$ is methyl.

18. A process according to claim 1, wherein R$^4$ is acyl having 1–15 C atoms.

19. A process according to claim 1, wherein R$^4$ is alkyl having 1–8 C atoms.

20. A process according to claim 1, wherein R$^4$ is 3,4-methylenedioxybenzoyl, 3,4,5-trimethoxybenzyl, isonicotinoyl or methyl.

21. A process for the resolution of enantiomers of 5-heteroaryl-1,3,4-thiadiazinones of formula I:

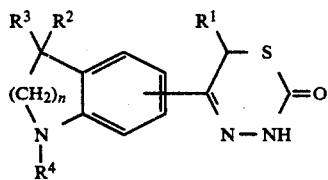

wherein
R¹ is A,
R² and R³ are each independently H or A,
R⁴ is H, A or acyl having 1-15 C atoms,
A is alkyl having 1-8 C atoms and
n is 1, 2 or 3,
by kinetic resolution of racemates thereof, said process comprising:

dissolving a racemate of compounds of formula I in an inert solvent or inert solvent mixture;

reacting said racemate with a chiral acid chloride;

reacting the resultant mixture of diastereoisomers with an amine or alcohol, thereby achieving a complete resolution of one of the diastereoisomers into the enantiomer on which it is based;

separating the resolved enantiomer from the unresolved diastereoisomer; and converting the unresolved diastereoisomer into its corresponding enantiomer by reaction with an amine or alcohol.

22. A process according to claim 21, wherein said resolved enantiomer separated from the unresolved diastereoisomer is contaminated with an amount of the corresponding other enantiomer which is removed by recrystallization.

* * * * *